(12) United States Patent
Kay et al.

(10) Patent No.: US 6,613,752 B2
(45) Date of Patent: Sep. 2, 2003

(54) METHODS OF IN VIVO GENE TRANSFER USING A SLEEPING BEAUTY TRANSPOSON SYSTEM

(75) Inventors: Mark A. Kay, Los Altos, CA (US); Steve Yant, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/927,886

(22) Filed: Aug. 10, 2001

(65) Prior Publication Data

US 2002/0103152 A1 Aug. 1, 2002

Related U.S. Application Data

(63) Continuation-in-part of application No. 09/440,301, filed on Nov. 17, 1999, now abandoned.
(60) Provisional application No. 60/162,279, filed on Oct. 28, 1999.

(51) Int. Cl.$^7$ .................. A01N 43/04; A01N 63/00; A61K 48/00; A61K 31/70; C12N 15/00
(52) U.S. Cl. ................ 514/44; 424/93.2; 435/320.1; 435/455; 435/463
(58) Field of Search .................. 514/44, 2; 435/320.1, 435/325, 455, 456, 463; 536/23.1

(56) References Cited

U.S. PATENT DOCUMENTS 5,719,055 A  *  2/1998  Cooper

FOREIGN PATENT DOCUMENTS

| WO | WO 98/40510 | * | 9/1998 |
| WO | WO 99/25817 |   | 5/1999 |

OTHER PUBLICATIONS

Raz et al. Transposition of the nematode *caenorgabditis elegans* Tc3 element in the zebrafish *danio rerio* vol. 8 No. 2 pp. 82–88 Sep. 4, 1997.*

Anderson et al. "Human gene therapy", *Nature*, 392(Supp.):25–30.

Dawson et al. (Jan. 1998), "Sleeping Beauty Awakes," *Nature Biotechnology*, vol. 16:20–21.

Ivics et al. (Nov. 14, 1997), "Molecular Reconstruction of *Sleeping Beauty*, a Tc1–like Transposon from Fish, and Its Transposition in Human Cells," *Cell*, vol. 91:501–510.

Luo et al. (Sep. 1998), "Chromosomal Transposition of a Tc1/Mariner–like Element in Mouse Embryonic Stem Cells," *Proc. Natl. Acad. Sci. USA*, vol. 95:10769–10773.

Raz et al. "Transposition of the nematode *Caenorhabditis elegans* Tc3 element in the zebrafish *Danio rerio*", *Current Biology*, vol. 8(2):82–88.

Schouten et al. (1998), "Transposon Tc1 of the Nematode *Caenorhabditis Elegans* Jumps in Human Cells," *Nucleic Acid Research*, vol. 26(12):3013–3017.

Verma and Somia, "Gene therapy–promises, problems and prospects", *Nature*, 389:239–242.

Zhang et al. (1998), "The *Himar1 Mariner* Transposase Cloned in a Recombinant Adenovirus Vector is Functional in Mammalian Cells," *Nucleic Acid Research*, vol. 26(16):3687–3693.

* cited by examiner

*Primary Examiner*—Deborah Crouch
(74) *Attorney, Agent, or Firm*—Bret E. Field; Bozicevic, Field & Francis

(57) ABSTRACT

Methods and compositions for introducing a nucleic acid into the genome of at least one cell of a multicellular organism are provided. In the subject methods, a Sleeping Beauty transposon that includes the nucleic acid is administered to the multicellular organism along with a source of a Sleeping Beauty transposase activity. Administration of the transposon and transposase results in integration of the transposon, as well as the nucleic acid present therein, into the genome of at least one cell of the multicellular organism The subject methods find use in a variety of different applications, including the in vivo transfer of genes for use in, among other applications, gene therapy applications.

33 Claims, 6 Drawing Sheets

SEQUENCE LISTING

```
<160> NUMBER OF SEQ ID NOS: 19

<210> SEQ ID NO 1
<211> LENGTH: 340
<212> TYPE: PRT
<213> ORGANISM: Artificial Sequence
<220> FEATURE:
<223> OTHER INFORMATION: recombinant transposase

<400> SEQUENCE: 1

Met Gly Lys Ser Lys Glu Ile Ser Gln Asp Leu Arg Lys Lys Ile Val
 1               5                  10                  15

Asp Leu His Lys Ser Gly Ser Ser Leu Gly Ala Ile Ser Lys Arg Leu
                20                  25                  30

Lys Val Pro Arg Ser Ser Val Gln Thr Ile Val Arg Lys Tyr Lys His
            35                  40                  45

His Gly Thr Thr Gln Pro Ser Tyr Arg Ser Gly Arg Arg Arg Val Leu
        50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly Arg Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
```

-continued

```
                130                 135                 140
Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Ser Ile
                180                 185                 190

Met Leu Trp Cys Gly Phe Ala Ala Gly Gly Thr Gly Ala Leu His Lys
                195                 200                 205

Ile Asp Gly Ile Met Arg Lys Glu Asn Tyr Val Asp Ile Leu Lys Gln
                210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
                260                 265                 270

Pro Asp Leu Asn Pro Ile Glu Asn Leu Trp Ala Glu Leu Lys Lys Arg
                275                 280                 285

Val Arg Ala Arg Arg Pro Thr Asn Leu Thr Gln Leu His Gln Leu Cys
                290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
                340

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
caaatggcca atgaccccaa gcat                                          24

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
gtcattggcc atttggaaga ccca                                          24

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
cgcatcgatg acggccagtg aatt                                          24

<210> SEQ ID NO 5
```

```
<211> LENGTH: 24
<212> TYPE: DNA
<213> ORGANISM: Artificial Sequence
<220> FEATURE:
<223> OTHER INFORMATION: primer

<400> SEQUENCE: 5
gccatcgatc aagcttgcat gcct                                          24

<210> SEQ ID NO 6
<211> LENGTH: 43
<212> TYPE: DNA
<213> ORGANISM: Artificial Sequence
<220> FEATURE:
<223> OTHER INFORMATION: primer

<400> SEQUENCE: 6
tatcgatact agtttaatta agatctcgag ctagcggccg ctg                     43

<210> SEQ ID NO 7
<211> LENGTH: 45
<212> TYPE: DNA
<213> ORGANISM: Artificial Sequence
<220> FEATURE:
<223> OTHER INFORMATION: primer

<400> SEQUENCE: 7
gcggccgcta gctcgagatc ttaattaaac tagtatcgat atgca                   45

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
agatgtccta actgacttgc c                                             21

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
gtggtgatcc taactgacct t                                             21

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
tacgccagct ggcgaaag                                                 18

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
```

```
agctcsctca ttaggcac                                              18

<210> SEQ ID NO 12
<211> LENGTH: 29
<212> TYPE: DNA
<213> ORGANISM: Artificial Sequence
<220> FEATURE:
<223> OTHER INFORMATION: transposon repeat sequence

<400> SEQUENCE: 12
gttcaagtcg aagtttaca tacacttag                                   29

<210> SEQ ID NO 13
<211> LENGTH: 30
<212> TYPE: DNA
<213> ORGANISM: Artificial Sequence
<220> FEATURE:
<223> OTHER INFORMATION: transposon repeat sequence

<400> SEQUENCE: 13
cagtgggtca gaagtttaca tacactaagg                                 30

<210> SEQ ID NO 14
<211> LENGTH: 31
<212> TYPE: DNA
<213> ORGANISM: Artificial Sequence
<220> FEATURE:
<223> OTHER INFORMATION: transposon repeat sequence

<400> SEQUENCE: 14
cagtgggtca gaagttaaca tacactcaat t                               31

<210> SEQ ID NO 15
<211> LENGTH: 30
<212> TYPE: DNA
<213> ORGANISM: Artificial Sequence
<220> FEATURE:
<223> OTHER INFORMATION: transposon repeat sequence

<400> SEQUENCE: 15
agttgaatcg gaagtttaca tacaccttag                                 30

<210> SEQ ID NO 16
<211> LENGTH: 33
<212> TYPE: DNA
<213> ORGANISM: Artificial Sequence
<220> FEATURE:
<223> OTHER INFORMATION: transposon repeat sequence

<400> SEQUENCE: 16
cagttgaggt caggaagttt acatacactt aag                             33

<210> SEQ ID NO 17
<211> LENGTH: 8
<212> TYPE: DNA
<213> ORGANISM: Artificial Sequence
<220> FEATURE:
<223> OTHER INFORMATION: transposon repeat sequence

<400> SEQUENCE: 17 acatacac                                                          8

<210> SEQ ID NO 18
<211> LENGTH: 226
<212> TYPE: DNA
```

```
<213> ORGANISM: Artificial Sequence
<220> FEATURE:
<223> OTHER INFORMATION: transposon repeat sequence

<400> SEQUENCE: 18
agttgaagtc ggaagtttac atacacttaa gttggagtca ttaaaactcg tttttcaact      60
acaccacaaa tttcttgtta acaaacaata gttttggcaa gtcagttagg acatctactt     120
tgtgcatgac acaagtcatt tttccaacaa ttgtttacag acagattatt tcacttataa    180
ttcactgtat cacaattcca gtgggtcaga agtttacata cactaa                   226

<210> SEQ ID NO 19
<211> LENGTH: 228
<212> TYPE: DNA
<213> ORGANISM: Artificial Sequence
<220> FEATURE:
<223> OTHER INFORMATION: transposon repeat sequence

<400> SEQUENCE: 19
ttgagtgtat gttaacttct gacccactgg gaatgtgatg aaagaaataa aagctgaaat      60
gaatcattct ctctactatt attctgatat ttcacattct taaaataaag tggtgatcct    120
aactgacctt aagacaggga atctttactc ggattaaatg tcaggaattg tgaaaaagtg    180
agtttaatgt atttggctaa ggtgtatgta aacttccgac ttcaactg                 228
```

METHODS OF IN VIVO GENE TRANSFER USING A SLEEPING BEAUTY TRANSPOSON SYSTEM

CROSS REFERENCE TO RELATED APPLICATIONS

This application is a continuation-in-part of application Ser. No. 09/440,301 filed Nov. 17, 1999 now abandoned which application claims priority to application Ser. No. 60/162,279 filed Oct. 28, 1999; the disclosures of which are herein incorporated by reference.

ACKNOWLEDGMENT

This invention was made with United States Government support under Grant No. NIH DR 49022 awarded by National Institutes of Health. The United States Government has certain rights in this invention.

INTRODUCTION

1. Field of the Invention

The field of this transformation.

2. Background of the Invention

The introduction of an exogenous nucleic acid sequence (e.g. DNA) into a cell, a process known as "transformation," plays a major role in a variety of biotechnology and related applications, including research, synthetic and therapeutic applications. Research applications in which transformation plays a critical role include the production of transgenic cells and animals. Synthetic applications in which transformation plays a critical role include the production of peptides and proteins. Therapeutic applications in which transformation plays a key role include gene therapy applications. Because of the prevalent role transformation plays in the above and other applications, a variety of different transformation protocols have been developed.

In many transformation applications, it is desirable to introduce the exogenous DNA in a manner such that it is incorporated into a target cell's genome. One means of providing for genome integration is to employ a vector that is capable of homologous recombination. Techniques that rely on homologous recombination can be disadvantageous in that the necessary homologies may not always exist; the recombination events may be slow, etc. As such, homologous recombination based protocols are not entirely satisfactory.

Accordingly, alternative viral based transformation protocols have been developed, in which a viral vector is employed to introduce exogenous DNA into a cell and then subsequently integrate the introduced DNA into the target cell's genome. Viral based vectors finding use include retroviral vectors, e.g. Moloney murine leukemia viral based vectors. Other viral based vectors that find use include adenovirus derived vectors, HSV derived vectors, sindbis derived vectors, etc. While viral vectors provide for a number of advantages, their use is not optimal in many situations. Disadvantages associated with viral based vectors include immunogenicity, viral based complications, and the like.

Accordingly, there is continued interest in the development of additional methods of integrating exogenous nucleic acid into the genome of a target cell for use in transformation protocols. Of particular interest is the development of a non-viral in vivo nucleic acid transfer protocol that provides for stable genome integration by a mechanism other than homologous recombination.

3. Relevant Literature

Patent applications of interest include: WO 98/40510 and WO 99/25817. Also of interest are: Dawson & Finnegan, Nat. Biotechnol. (1998) 16:20–21; Ivics et al., Cell (1997) 91: 501–510; Ivics et al., Proc. Nat'l Acad. Sci. USA (1996) 93:5008–5013; Luo et al., Proc. Nat'l Acad. Sci USA (1998) 95:10769–10773; Schouten et al., Nuc. Acids Res. (1998) 26:3013–3017; Zhang et al., Nuc. Acids Res. (1998) 26:3687–3693.

SUMMARY OF THE INVENTION

Methods and compositions for introducing an exogenous nucleic acid into the genome of at least one cell of a multicellular organism are provided. In the subject methods, a Sleeping Beauty transposon that includes the exogenous nucleic acid is administered to the multicellular organism along with a source of a Sleeping Beauty transposase activity. Following administration, the exogenous nucleic acid is integrated into the genome of at least one cell of the multicellular organism. The subject methods find use in a variety of different applications, including the in vivo transfer of a gene into a target cell e.g. for use in gene therapy applications.

DESCRIPTION OF THE SPECIFIC EMBODIMENTS

Figure 1A:
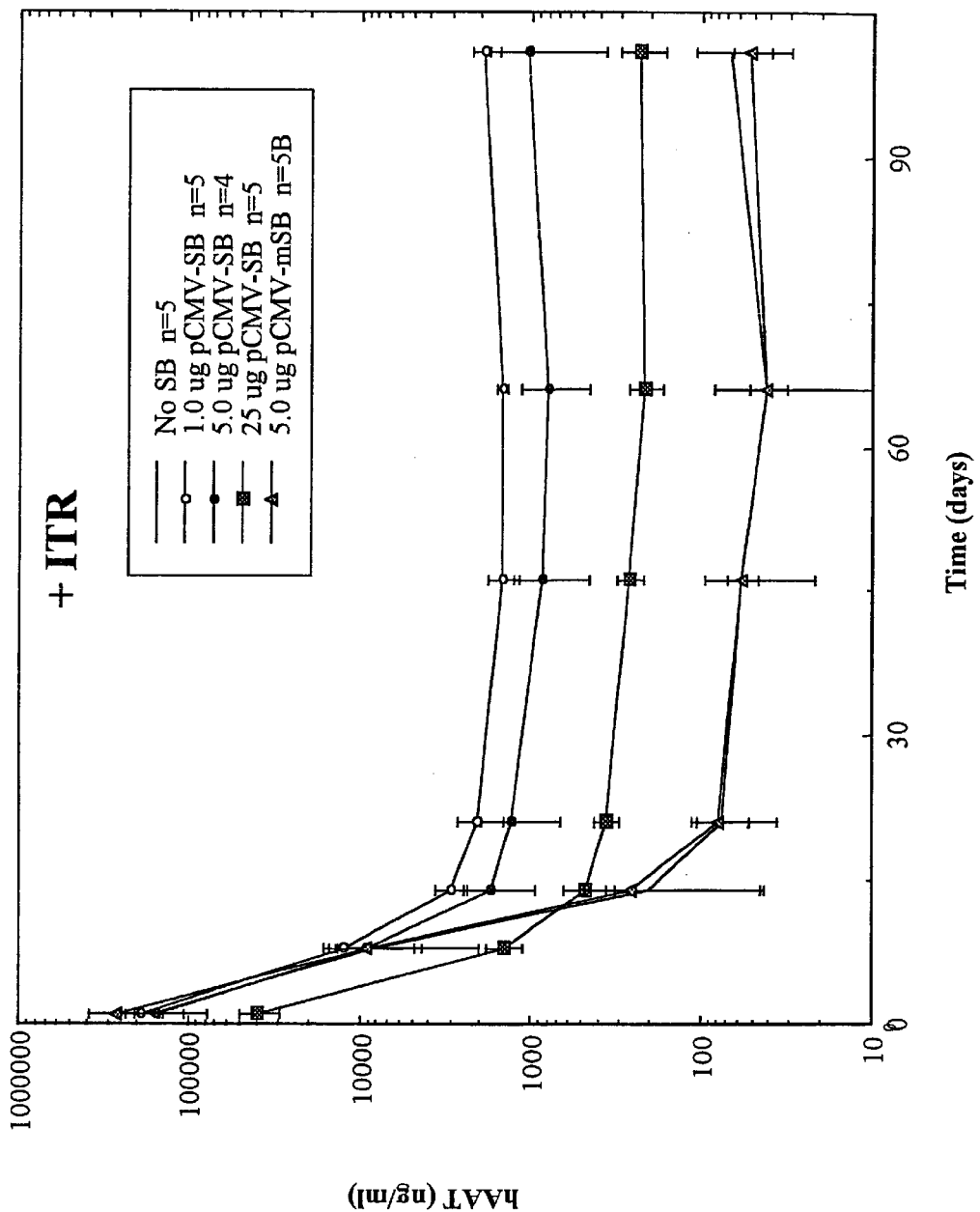
FIGS. 1A to 1C provide the results from various in vivo gene transfer experiments, as described in greater detail in the experimental section, infra.

Methods and compositions for introducing an exogenous nucleic acid into the genome of at least one cell of a multicellular organism are provided. In the subject methods, a Sleeping Beauty transposon system that includes a source of Sleeping Beauty transposase activity and a Sleeping Beauty transposon containing the exogenous nucleic acid are administered directly to the multicellular organism. In vivo administration results in integration of the transposon, and consequently the exogenous nucleic acid, into at least one target cell of the multicellular organism. The subject methods find use in a variety of different applications, including in vivo gene transfer for use in, e.g. gene therapy applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

General Introduction

As summarized above, the present invention provides methods of introducing exogenous nucleic acid into the genome of at least one cell, i.e. a target cell, of a multicellular organism. A critical feature of the subject invention is that the subject methods are in vivo methods, by which is meant that the exogenous nucleic acid is administered directly to the multicellular organism, in contrast to in vitro methods in which the target cell or cells are removed from the multicellular organism and then contacted with the exogenous nucleic acid. Essential to the subject methods is the use of a Sleeping Beauty transposon system to integrate the exogenous nucleic acid into the target cell following in vivo administration. By Sleeping Beauty transposon system is meant a collection of components that at least includes a Sleeping Beauty transposon and a source of Sleeping Beauty transposase activity.

Sleeping Beauty Transposon System

As indicated above, the Sleeping Beauty transposon systems employed in the subject methods at least include a Sleeping Beauty transposon and a source of a Sleeping Beauty transposase activity. By Sleeping Beauty transposon is meant a nucleic acid that is flanked at either end by inverted repeats which are recognized by an enzyme having Sleeping Beauty transposase activity. By 'recognized' is meant that a Sleeping Beauty transposase is capable of binding to the inverted repeat and then integrating the trarsposon flanked by the inverted repeat into the genome of the target cell. Representative inverted repeats that may be found in the Sleeping Beauty transposons of the subject methods include those disclosed in WO 98/40510 and WO 99/25817. Of particular interest are inverted repeats that are recognized by a transposase that shares at least about 80% amino acid identity to SEQ ID NO:01 of WO 99/25817, which is:

```
                                          (seq id no:01)
MGKSKEISQD LRKKIVDLHK SGSSLGAISK RLKVPRSSVQ
TIVRKYKHHG TTQPSYRSGR RRVLSPRDER TLVRKVQINP
RTTAKDLVKM LEETGTKVSI STVKRVLYRH NLKGRSARKK
PLLQNRHKKA RLRFATAHGD KDRTFWRNVL WSDETKIELF
GHNDHRYVWR KKGEACKPKN TIPTVKHGGG SIMLWCGFAA

GGTGALHKID GIMRKENYVD ILKQHLKTSV RKLKLGRKWV

FQMDNDPKHT SKVVAKWLKD NKVKVLEWPS QSPDLNPIEN

LWAELKKRVR ARRPTNLTQL HQLCQEEWAK IHPTYCGKLV

EGYPKRLTQV KQFKGNATKY
```

In many embodiments, each inverted repeat of the transposon includes at least one direct repeat. The transposon element is a linear nucleic acid fragment that can be used as a linear fragment or circularlized, for example in a plasmid. In certain embodiments, there are two directe repeats in each inverted repeat sequence. Direct repeat sequences of interest include:

The 5' outer repeat:

```
5'-GTTCAAGTCGGAAGTTTACATACACTTAG-3'  (seq id no:12)
```

The 5' inner repeat:

```
5'-CAGTGGGTCAGAAGTTTACATACACTAAGG-3'  (seq id no:13)
```

The 3' inner repeat:

```
5'-CAGTGGGTCAGAAGTTAACATACACTCAATT-3'     (seq id
                                           no:14)
```

The 3' outer repeat:

```
5'-AGTTGAATCGGAAGTTTACATACACCTTAG-3'  (seq id no:15)
```

A consensus sequence of interest is:

```
                                          (seq id no:16)
5'-CA(GT)TG(AG)GTC(AG)GAAGTTTACATACACTTAAG-3'
```

In one embodiment, a direct repeat sequence of interest includes at least the following sequence:
ACATACAC (seq id no:17)

In certain embodiments, the inverted repeat sequence is:

```
                                          (seq id no:18)
5'-AGTTGAAGTC GGAAGTTTAC ATACACTTAA GTTGGAGTCA

TTAAAACTCG TTTTTCAACT ACACCACAAA TTTCTTGTTA

ACAAACAATA GTTTTGGCAA GTCAGTTAGG ACATCTACTT

TGTGCATGAC ACAAGTCATT TTTCCAACAA TTGTTTACAG

ACAGATTATT TCACTTATAA TTCACTGTAT CACAATTCCA

GTGGGTCAGA AGTTTACATA CACTAA-3'
``` and a second inverted repeat is:

```
                                          (seq id no:19)
5'-TTGAGTGTAT GTTAACTTCT GACCCACTGG GAATGTGATG

AAAGAAATAA AAGCTGAAAT GAATCATTCT CTCTACTATT

ATTCTGATAT TTCACATTCT TAAAATAAAG TGGTGATCCT

AACTGACCTT AAGACAGGGA ATCTTTACTC GGATTAAATG

TCAGGAATTG TGAAAAAGTG AGTTTAATG TATTTGGCTA

AGGTGTATGT AAACTTCCGA CTTCAACTG-3'.
```

The above specific sequences are also provided in the priority applications of WO 98/40510, the disclosures of which are herein incorporated by reference.

```
GGTGALHKID GIMRKENYVD ILKQHLKTSV RKLKLGRKWV FQMDNDPKHT

SKVVAKWLKD NKVKVLEWPS QSPDLNPIEN LWAELKKRVR ARRPTNLTQL

HQLCQEEWAK IHPTYCGKLV EGYPKRLTQV KQFKGNATKY
```

In the subject Sleeping Beauty transposons, the Sleeping Beauty transposase recognized inverted repeats flank an insertion nucleic acid, i.e. a nucleic acid that is to be inserted into a target cell genome, as described in greater detail below. The subject transposons may include a wide variety of insertion nucleic acids, where the nucleic acids may include a sequence of bases that is endogenous and/or exogenous to the multicellular organism, where an exogenous sequence is one that is not present in the target cell while an endogenous sequence is one that pre-exists in the target cell prior to insertion. In any event, the nucleic acid of the transposon is exogenous to the target cell, since it originates at a source other than the target cell and is introduce into the cell by the subject methods, as described infra. The nature of the nucleic acid will vary depending on the particular protocol being performed. For example, in research applications the exogenous nucleic acid may be a novel gene whose protein product is not well characterized. In such applications, the transposon is employed to stably introduce the gene into the target cell and observe changes in the cell phenotype in order to characterize the gene. Alternatively, in protein synthesis applications, the exogenous nucleic acid encodes a protein of interest which is to be produced by the cell. In yet other embodiments where the transposon is employed, e.g. in gene therapy, the exogenous nucleic acid is a gene having therapeutic activity, i.e. a gene that encodes a product of therapeutic utility. Another way to refer to the insertion nucleic acid of the transposon is as the "inter inverted repeat domain" of the transposon. The inter inverted repeat domain of the Sleeping Beauty transposon, i.e. that domain or region of the transposon located or positioned between the flanking inverted repeats, may vary greatly in size. The only limitation on the size of the inverted repeate is that the size should not be so great as to inactivate the ability of the transposon system to integrate the transposon into the target genome. The upper and lower limits of the size of this inter inverted repeat domain may readily be determined empirically by those of skill in the art.

A variety of different features may be present in the inter inverted repeat domain of the Sleeping Beauty transposon. In many embodiments, the inter inverted repeat domain is characterized by the presence of at least one transcriptionally active gene. By transcriptionally active gene is meant a coding sequence that is capable of being expressed under intracellular conditions, e.g. a coding sequence in combination with any requisite expression regulatory elements that are required for expression in the intracellular environment of the target cell whose genome is modified by integration of the transposon. As such, the transcriptionally active genes of the subject vectors typically include a stretch of nucleotides or domain, i.e. expression module, that includes a coding sequence of nucleotides in operational combination, i.e. operably linked, with requisite transcriptional mediation or regulatory element(s). Requisite transcriptional mediation elements that may be present in the expression module include promoters, enhancers, termination and polyadenylation signal elements, splicing signal elements, and the like.

Preferably, the expression module includes transcription regulatory elements that provide for expression of the gene in a broad host range. A variety of such combinations are known, where specific transcription regulatory elements include: SV40 elements, as described in Dijkema et al., EMBO J. (1985) 4:761; transcription regulatory elements derived from the LTR of the Rous sarcoma virus, as described in Gorman et al., Proc. Nat'l Acad. Sci USA (1982) 79:6777; transcription regulatory elements derived from the LTR of human cytomegalovirus (CMV), as described in Boshart et al., Cell (1985) 41:521; hsp70 promoters, (Levy-Holtzman, R. and I. Schechter (Biochim. Biophys. Acta (1995) 1263: 96–98) Presnail, J. K. and M. A. Hoy, (Exp. Appl. Acarol. (1994) 18: 301–308)) and the like.

In certain embodiments, the at least one transcriptionally active gene or expression module present in the inter inverted repeat domain acts as a selectable marker. A variety of different genes have been employed as selectable markers, and the particular gene employed in the subject vectors as a selectable marker is chosen primarily as a matter of convenience. Known selectable marker genes influx: the thimydine kinase gene, the dihydrofolate reductase gene, the xanthine-guanine phosporibosyl transferase gene, CAD, the adenosine deaminase gene, the asparagine synthetase gene, the antibiotic resistance genes, e.g. $tet^r$, $amp^r$, $Cm^r$or cat, $kan^r$ or $neo^r$ (aminoglycoside phosphotransferase genes), the hygromycin B phosphotransferase gene, genes whose expression provides for the presence of a detectable product, either directly or indirectly, e.g. β-galactosidase, GFP, and the like.

In many embodiments, the at least one transcriptionally active gene or module encodes a protein that has therapeutic activity for the multicellular organism, where such include genes encoding the following products: factor VIII, factor IX, β-globin, low-density protein receptor, adenosine deaminase, purine nucleoside phosphorylase, sphingomyelinase, glucocerebrosidase, cystic fibrosis transmembrane regulator, α-antitrypsin, CD-18, ornithine transcarbamylase, arginosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, interleukins, cytokines, small peptides etc, and the like In addition to the at least one transcriptionally active gene, the inverted repeat domain of the subject transposons also typically include at least one restriction endonuclease recognized site, e.g. restriction site, located between the flanking inverted repeats, which serves as a site for insertion of an exogenous nucleic acid. A variety of restriction sites are known in the art and may be included in the inter inverted repeat domain, where such sites include those recognized by the following restriction enzymes: HindIII, PstI, SalI, AccI, HincII, XbaI, BamHI, SmaI, XmaI, KpnI, SacI, EcoRI, and the like. In many embodiments, the vector includes a polylinker, i.e. a closely arranged series or array of sites recognized by a plurality of different restriction enzymes, such as those listed above.

As mentioned above, the subject Sleeping Beauty transposon system also includes a source of Sleeping Beauty transposase activity. The Sleeping Beauty transposase activity is one that binds to the inverted repeats of the Sleeping Beauty transposon and mediates integration of the transposon into the genome of the target cell. Any suitable Sleeping Beauty transposase activity may be employed in the subject methods so long as it meets the above parameters, where suitable Sleeping Beauty transposase activities are disclosed in WO 98/40510 and WO 99/25817, the disclosures of which are herein incorporated by reference, including the specific Sleeping Beauty transpoposase having an amino acid sequence of SEQ ID NO:01.

The source of Sleeping Beauty transposase activity may vary. In certain embodiments, the source may be a protein that exhibits Sleeping Beauty transposase activity. However, the source is generally a nucleic acid that encodes a protein having Sleeping Beauty transposase activity. Where the source is a nucleic acid which encodes a protein having Sleeping Beauty transposase activity, the nucleic acid encoding the transposase protein is generally part of an expression module, as described above, where the additional elements provide for expression of the transposase as required.

The subject Sleeping Beauty transposon is generally present on a vector which is administered to the multicellular organism, as described in greater detail below. The transposon may be present on a variety of different vectors, where representative vectors include plasmids, viral based vectors, linear DNA molecules and the like, where representative vectors are described infra in greater detail.

In certain embodiments where the source of transposase activity is a nucleic acid, the Sleeping Beauty transposon and the nucleic acid encoding the transposase are present on separate vectors, e.g. separate plasmids. In certain other embodiments, the transposase encoding domain may be present on the same vector as the transposon, e.g. on the same plasmid. When present on the same vector, the Sleeping Beauty transposase encoding region or domain is located outside the inter inverted repeat flanked domain. In other words, the transposase encoding region is located external to the region flanked by the inverted repeats, i.e. outside the inter inverted repeat domain described supra. Put another way, the tranposase encoding region is positioned to the left of the left terminal inverted repeat or the right of the right terminal inverted repeat.

Methods of Preparing the Subject Sleeping Beauty Transposon System

The various elements of the Sleeping Beauty Transposon System employed in the subject methods, e.g. the vector(s) of the subject invention, may be produced by standard methods of restriction enzyme cleavage, ligation and molecular cloning. One protocol for constructing the subject vectors includes the following steps. First, purified nucleic acid fragments containing desired component nucleotide sequences as well as extraneous sequences are cleaved with restriction endonucleases from initial sources, e.g. a vector comprising the Sleeping Beauty transposase gene. Fragments containing the desired nucleotide sequences are then separated from unwanted fragments of different size using conventional separation methods, e.g., by agarose gel electrophoresis. The desired fragments are excised from the gel and ligated together in the appropriate configuration so that a circular nucleic acid or plasmid containing the desired sequences, e.g. sequences corresponding to the various elements of the subject vectors, as described above is produced. Where desired, the circular molecules so constructed are then amplified in a prokaryotic host, e.g. *E. coli*. The procedures of cleavage, plasmid construction, cell transformation and plasmid production involved in these steps are well known to one skilled in the art and the enzymes required for restriction and ligation are available commercially. (See, for example, R. Wu, Ed., Methods in Enzymology, Vol. 68, Academic Press, N.Y. (1979); T. Maniatis, E. F. Fritsch and J. Sambrook, Molecular Cloning: A Laboratory Manual, Cold Spring Harbor Laboratory Press, Cold Spring Harbor, N.Y. (1982); Catalog 1982–83, New England Biolabs, Inc.; Catalog 1982–83, Bethesda Research Laboratories, Inc. An example of how to construct the vectors employed in the subject methods is provided in the Experimental section, infra. The preparation of a representative Sleeping Beauty transposon system is also disclosed in WO 98/40510 and WO 99/25817.

Methods of Using the Sleeping Beauty Transposon System to Integrate a Nucleic Acid into a Target Cell Genome The subject methods find use in a variety of applications in which it is desired to introduce and stably integrate an exogenous nucleic acid into the genome of a target cell. As mentioned above, a critical feature of the subject methods is that the vector or vectors comprising the various elements of the Sleeping Beauty transposon system, e.g. plasmids, are administered to a multicellular organism that includes the target cell, i.e. the cell into which integration of the nucleic acid of the transposon is desired. By multicellular organism is meant an organism that is not a single celled organism. Multicellular organisms of interest include plants and animals, where animals are of particular interest. Animals of interest include vertebrates, where the vertebrate is a mammal in many embodiments. Mammals of interest include; rodents, e.g. mice, rats; livestock, e.g. pigs, horses, cows, etc., pets, e.g. dogs, cats; and primates, e.g. humans. As the subject methods involve administration of the transposon system directly to the multicellular organism, they are in vivo methods of integrating the exogenous nucleic acid into the target cell.

The route of administration of the Sleeping Beauty transposon system to the multicellular organism depends on several parameters, including: the nature of the vectors that carry the system components, the nature of the delivery vehicle, the nature of the multicellular organism, and the like, where a common feature of the mode of administration is that it provides for in vivo delivery of the transposon system components to the target cell(s). In certain embodiments, linear or circularized DNA, e.g. a plasmid, is employed as the vector for delivery of the transposon system to the target cell. In such embodiments, the plasmid may be administered in an aqueous delivery vehicle, e.g. a saline solution. Alternatively, an agent that modulates the distribution of the vector in the multicellular organism may be employed. For example, where the vectors comprising the subject system components are plasmid vectors, lipid based, e.g. liposome, vehicles may be employed, where the lipid based vehicle may be targeted to a specific cell type for cell or tissue specific delivery of the vector. Patents disclosing such methods include: U.S. Pat. Nos. 5,877,302; 5,840,710; 5,830,430; and 5,827,703, the disclosures of which are herein incorporated by reference. Alternatively, polylysine based peptides may be employed as carriers, which may or may not be modified with targeting moieties, and the like. (Brooks, A. I., et al. 1998, J. Neurosci. Methods V. 80 p: 137–47; Muramatsu, T., Nakamura, A., and H. M. Park 1998, Int. J. Mol. Med. V. 1 p: 55–62). In yet other embodiments, the system components may be incorporated onto viral vectors, such as adenovirus derived vectors, sindbis virus derived vectors, retroviral derived vectors, etc. hybrid vectors, and the like. The above vectors and delivery vehicles are merely representative. Any vector/delivery vehicle combination may be employed, so long as it provides for in vivo administration of the transposon system to the multicellular organism and target cell.

Because of the multitude of different types of vectors and delivery vehicles that may be employed, administration may be by a number of different routes, where representative routes of administration include: oral, topical, intraarterial, intravenous, intraperitoneal, intramuscular, etc. The particular mode of administration depends, at least in part, on the nature of the delivery vehicle employed for the vectors which harbor the Sleeping Beauty transposons system. In many embodiments, the vector or vectors harboring the Sleeping Beauty transposase system are administered intravascularly, e.g. intraarterially or intravenously, employing an aqueous based delivery vehicle, e.g. a saline solution.

The elements of the Sleeping Beauty transposase system, e.g. the Sleeping Beauty transposon and the Sleeping Beauty transposase source, are administered to the multicellular organism in an in vivo manner such that they are introduced into a target cell of the multicellular organism under conditions sufficient for excision of the inverted repeat flanked nucleic acid from the vector carrying the transposon and subsequent integration of the excised nucleic acid into the genome of the target cell. As the transposon is introduced into the cell "under conditions sufficient for excision and integration to occur," the subject method further includes a step of ensuring that the requisite Sleeping Beauty transposase activity is present in the target cell along with the introduced transposon. Depending on the structure of the transposon vector itself, i.e. whether or not the vector includes a region encoding a product having Sleeping Beauty transposase activity, the method may further include introducing a second vector into the target cell which encodes the requisite transposase activity, where this step also includes an in vivo administration step.

The amount of vector nucleic acid comprising the transposon element, and in many embodiments the amount of vector nucleic acid encoding the transposase, that is introduced into the cell is sufficient to provide for the desired excision and insertion of the transposon nucleic acid into the target cell genome. As such, the amount of vector nucleic acid introduced should provide for a sufficient amount of transposase activity and a sufficient copy number of the nucleic acid that is desired to be inserted into the target cell. The amount of vector nucleic acid that is introduced into the target cell varies depending on the efficiency of the particular introduction protocol that is employed, e.g. the particular in vivo administration protocol that is employed.

The particular dosage of each component of the system that is administered to the multicellular organism varies depending on the nature of the transposon nucleic acid, e.g. the nature of the expression module and gene, the nature of the vector on which the component elements are present, the nature of the delivery vehicle and the like. Dosages can readily be determined empirically by those of skill in the art. For example, in mice where the Sleeping Beauty Transposase system components are present on separate plasmids which are intravenously administered to a mammal in a saline solution vehicle, the amount of transposon plasmid that is administered in many embodiments typically ranges from about 0.5 to 40 and is typically about 25 $\mu$g, while the amount of Sleeping Beauty transposase encoding plasmid that is administered typically ranges from about 0.5 to 25 and is usually about 1 $\mu$g.

Once the vector DNA has entered the target cell in combination with the requisite transposase, the nucleic acid region of the vector that is flanked by inverted repeats, i.e. the vector nucleic acid positioned between the Sleeping Beauty transposase recognized inverted repeats, is excised from the vector via the provided transposase and inserted into the genome of the targeted cell. As such, introduction of the vector DNA into the target cell is followed by subsequent transposase mediated excision and insertion of the exogenous nucleic acid carried by the vector into the genome of the targeted cell.

The subject methods may be used to integrate nucleic acids of various sizes into the target cell genome. Generally, the size of DNA that is inserted into a target cell genome using the subject methods ranges from about 0.5 kb to 10.0 kb, usually from about 1.0 kb to about 8.0 kb.

The subject methods result in stable integration of the nucleic acid into the target cell genome. By stable integration is meant that the nucleic acid remains present in the target cell genome for more than a transient period of time, and is passed on a part of the chromosomal genetic material to the progeny of the target cell. The subject methods of stable integration of nucleic acids into the genome of a target cell find use in a variety of applications in which the stable integration of a nucleic acid into a target cell genome is desired. Applications in which the subject vectors and methods find use include: research applications, polypeptide synthesis applications and therapeutic applications. Each of these representative categories of applications is described separately below in greater detail.

Research Applications

Examples of research applications in which the subject methods of nucleic acid integration find use include applications designed to characterize a particular-gene. In such applications, the subject transposon system is employed to insert a gene of interest into a target cell and the resultant effect of the inserted gene on the cell's phenotype is observed. In this manner, information about the gene's activity and the nature of the product encoded thereby can be deduced. The subject transposon systems can also be employed to identify and define DNA sequences that control gene expression, e.g. in a temporal (e.g. certain developmental stage) or spatial (e.g. particular cell or tissue type) manner. In such assays, the subject transposons are employed to stably integrate into the genome of a target cell via in vivo transfer a selectable marker gene, e.g. antibiotic resistance, LacZ, etc., where the transposon lacks a sufficient promoter for the marker gene such that the marker is not significantly expressed, if at all, unless it is underneath an endogenous promoter element. If the maker gene is inserted into the target cell genome in sufficient relationship to an endogenous promoter sequence, it will be expressed. From the resultant expression profile of the marker gene, the endogenous promoter that is mediating its expression can then be characterized. The subject methods can also be used to study integration mutants, where a gene of interest is inserted randomly into the genome and the effects of this random insertion on the targeted cell phenotype are observed. One can also employ the subject methods to produce models in which overexpression and/or misexpression of a gene of interest is produced in a cell and the effects of this mutant expression pattern are observed. One can also use the subject methods to readily clone genes introduced into a host cell via insertional mutagenesis that yields phenotypes and/or expression patterns of interest. In such applications, the subject transposon systems are employed to generate insertional mutants through random integration of DNA. The phenotype and/or expression pattern of the resultant mutant is then assayed using any convenient protocol. In those mutants of interest, cloning of the DNA associated with the phenotype and/or expression pattern of interest is readily accomplished through use of the inverted repeats of the transposon.

Polypeptide Synthesis Applications

In addition to the above research applications, the subject methods also find use in the synthesis of polypeptides, e.g. proteins of interest. In such applications, a transposon that includes a gene encoding the polypeptide of interest in combination with requisite and/or desired expression regulatory sequences, e.g. promoters, etc., (i.e. an expression module) is introduced into the target cell, via in vivo administration to the multicellular organism in which the target cell resides, that is to serve as an expression host for expression of the polypeptide. Following in vivo administration and subsequent stable integration into the target cell genome, the multicellular organism, and targeted host cell present therein, is then maintained under conditions sufficient for expression of the integrated gene. The expressed protein is then harvested, and purified where desired, using any convenient protocol.

As such, the subject methods provide a means for at least enhancing the amount of a protein of interest in a multicellular organism. The term 'at least enhance' includes situations where the methods are employed to increase the amount of a protein in a multicellular organism where a certain initial amount of protein is present prior to in vivo administration of the transposon system. The term 'at least enhance' also includes those situations in which the multicellular organism includes substantially none of the protein prior to administration of the transposon system. As the subject methods find use in at least enhancing the amount of a protein present in a multicellular organism, they find use in a variety of different applications, including agricultural applications, pharmaceutical preparation applications, and the like, as well as therapeutic applications, described in greater detail infra.

Therapeutic Applications

The subject methods also find use in therapeutic applications, in which the transposon systems are employed to stably integrate a therapeutic nucleic acid, e.g. gene, into the genome of a target cell, i.e. gene therapy applications. The subject transposon systems may be used to deliver a wide variety of therapeutic nucleic acids. Therapeutic nucleic acids of interest include genes that replace defective genes in the target host cell, such as those responsible for genetic defect based diseased conditions; genes which have therapeutic utility in the treatment of cancer; and the like. Specific therapeutic genes for use in the treatment of genetic defect based disease conditions include genes encoding the following products: factor VIII, factor IX, β-globin, low-density protein receptor, adenosine deaminase, purine nucleoside phosphorylase, sphingomyelinase, glucocerebrosidase, cystic fibrosis transmembrane regulator, α-antitrypsin, CD-18, ornithine transcarbamylase, arginosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, and the like. Cancer therapeutic genes that may be delivered via the subject methods include: genes that enhance the antitumor activity of lymphocytes, genes whose expression product enhances the immunogenicity of tumor cells, tumor suppressor genes, toxin genes, suicide genes, multiple-drug resistance genes, antisense sequences, and the like. The subject methods can be used to not only introduce a therapeutic gene of interest, but also any expression regulatory elements, such as promoters, and the like, which may be desired so as to obtain the desired temporal and spatial expression of the therapeutic gene.

An important feature of the subject methods, as described supra, is that the subject methods may be used for in vivo gene therapy applications. By in vivo gene therapy applications is meant that the target cell or cells in which expression of the therapeutic gene is desired are not removed from the host prior to contact with the transposon system. In contrast, vectors that include the transposon system are administered directly to the multicellular organism and are taken up by the target cells, following which integration of the gene into the target cell genome occurs.

The following examples are offered by way of illustration and not by way of limitation.

Experimental

I. Plasmid Construction

A. pCMV-mSB, Which Encoded Catalytically Inactive Transposase.

The aspartate->alanine (D244E) mutation was introduced into the catalytic domain of Sleeping Beauty by polymerase chain reaction (PCR). The oligonucleotide primers DA1 (5'-CAAATGGCCAATGACCCCAAGCAT) (SEQ ID NO:02) and DA2 (5'-GTCATTGGCCATTT GGAAGACCCA) (SEQ ID NO:03) were used in conjunction with CL1 (5'-CGCATCGATGACGGCCAGTGAATT) (SEQ ID NO:04) and CL2 (5'-GCCATCGATC AAGCTTGCATGCCT) (SEQ ID NO:05) to generate a 1.0-kb product. PCR products were digested with BamH I and EcoR I, cloned into a derivative of pcDNA3 (InVitrogen) containing a 2.2-kb Pvu II—Pvu II NEO deletion (pcDNA3-N), and sequenced.

B. Transposon Construction.

pThAAT was generated by replacing the Nsi I-Bsm I region of pTNEO with the 2.0-kb Xho I—Xho I fragment from pBS-RSV-hAAT-bpA. For construction of pTRSV-βGeo, the 1.4-kb Hind III-Xma I hAAT cDNA in pBS-RSV-hAAT-bpA was replaced with the 4.3-kb Hind III fragment from pSAβGeolox2dta (kindly provided by Phil Soriano) to create pRSV-βGeo, from which a 5.0-kb Xho I—Xho I fragment was excised and inserted into the Nsi I-Bsm I region of pTNEO. pTNori and pTNorisacB were made by replacing the origin-minus Neo cassette in pTNEO with the 2.2-kb Avr II-Bsm I fragment from pAAV-Snori, followed by Xba I-Sal I ligation with the 1.7-kb sacB gene from pSWU31 encoding bacterial sucrose lethality. pTEF1α-hFIX was constructed by Not I-Spe I ligation of the 4.7-kb fragment from pAAV-EF1α-hFIX with the plasmid pT-MCS, which was engineered to contain nine unique restriction sites (Nsi I, Cla I, Spe I, Pac I, Bgl II, Xho I, Nhe I, Not I, Bsm I) between the transposon terminal repeats by replacing the 1.4-kb Nsi I-Bsm I fragment in pTNeo with annealed oligonucleotide primers MCS1 (5'-TATCGATACTAGTTTAATTAAGATCTCGAGCTAGCG GCCGCTG) (SEQ ID NO:06) and MCS2 (5'-GC GGC-CGCTAGCTCGAGATCTTAATTAAACTAGTATC GATATGCA) (SEQ ID NO:07). pCMV-GFP encoding the green fluorescent protein was constructed by inserting the 0.8-kb Pst I-Not I fragment from pEGFP-N1 (Clontech) into pcDNA-N.

II. Production and Integrative Capacity of Mutant Transposase in Cultured Human Cells.

Three vectors were employed, i.e., a vector encoding a neomycin (NEO) transposon (pTNori), a vector encoding the transposase (pCMV-SB) (Z. Ivics, et al, Cell 91, 501 (1997), and the plasmid pCMV-mSB, which contains a missense mutation (D244A) in a conserved catalytic triad (DDE motif). These vectors, as well as others, were to be utilized for many in vivo studies in mice, and thus had to be first tested in cultured mammalian cells for both expression and their capacity to support transposition of a foreign gene into mammalian chromosomes.

A western blot analysis for transposase expression in Hela cell extracts was performed. Hela cells were transfected with pCMV-SB or pCMV-mSB and total protein was isolated therefrom. The total protein was separated by SDS-PAGE, blotted to nitrocellulose membrane and probed with a polyclonal antibody to SB (kindly provided by Zoltan Ivics and Zsusanna Izsvak). The observed results indicate that both wild-type and mutant transposase are expressed to appreciable levels in the cell.

In another set of experiments, the transposition efficiency of the 3.4-kb NEO transposon encoded by pTNori was assessed in cultured human cells using plasmids encoding wild-type or mutant transposase. $5 \times 10^5$ Hela cells were co-transfected with pTNori and (a) pCMV-GFP, (b) pCMV- SB or (c) pCMV-mSB using Superfect (Qiagen). Cells were trypsinized 48 hours later, plated at 1/50 and 1/500 dilutions and selected for growth in DMEM containing G418 (500 ug/ml) for 14 days. G418-resistant (G418$^R$) foci were fixed and stained with methylene blue. A single representative dish from triplicate transfections is shown together with the corresponding number of G418$^R$ foci/dish.

The observed results show that, under these experimental conditions, tranposase can mediate transposition of foreign genes in ≧10% of transfected cells. Indeed, plasmid recovery strategies verified transposition occurred into TA dinucleotides at a variety of genomic loci in HeLa cells (data not shown). Finally, the results demonstrate that a D244A mutation in the carboxy-terminus of the transposase completely ablates the catalytic activity of the transposase in cultured cells, providing a crucial control for in vivo expression studies.

III. Transposase Can Maintain Long-Term Expression of Therapeutic Genes from Transposon-Based Vectors in Mice.

Figure 1B:
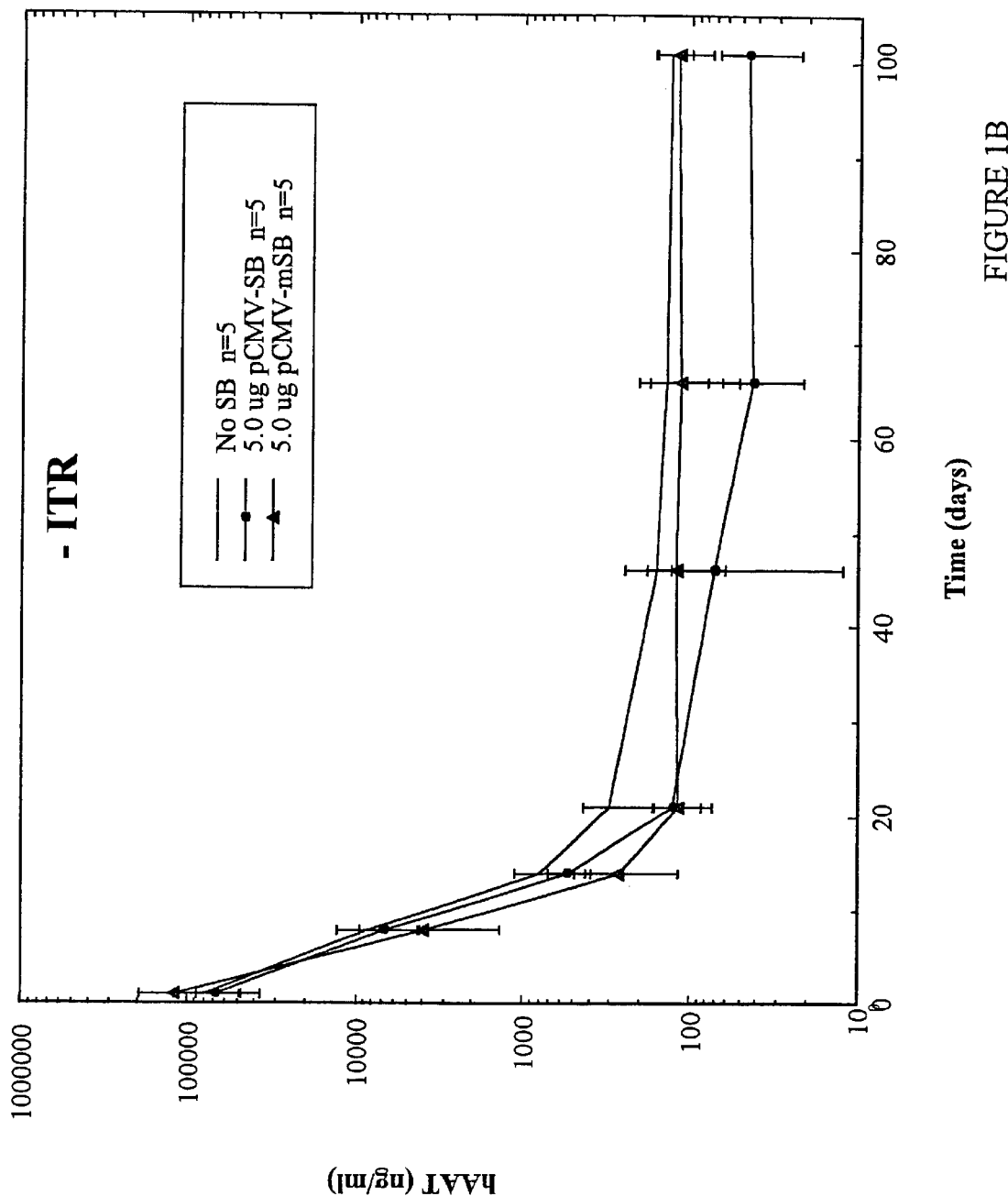
Figure 1C:
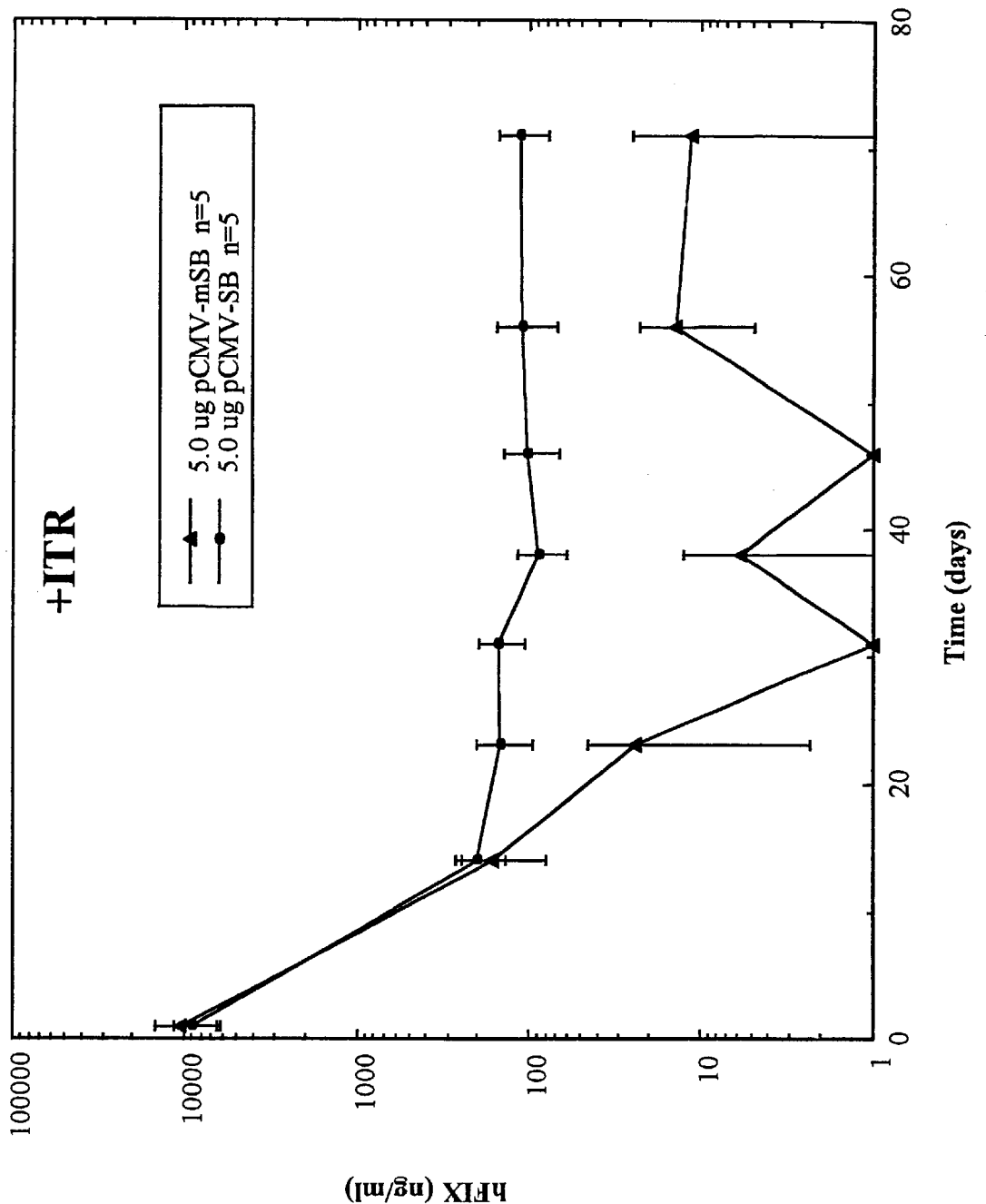

Plasmid DNA was delivered systemically to 6 week old C57B1/6 mice by a rapid 2 ml injection of 0.85% saline into the tail vein (F. Liu, Y. K. Song and D. Liu, Gene Therapy 6, 1258 (1999). Mice were bled at the indicated number of days after plasmid administration and the serum hAAT and HFIX concentrations determined by an ELISA assay {M. A. Kay, et al., Hum. Gene Ther. 3, 641 (1992); J. Walter, et al., Proc. Natl. Acad. Sci. U. S. A. 93, 3056 (1996)}. Values represent the mean+/−standard deviation. FIG. 1A) Average serum HAAT levels in mice receiving a TR-flanked HAAT cassette (pThAAT) and plasmids encoding transposase (pCMV-SB or pCMV-mSB). Animals were injected with 25 ug pThAAT together with 25 ug pcDNA3 (—), 5 ug mutant transposase (pCMV-mSB)+20 ug pcDNA3 ( ), or 1 ug, 5 ug, 25 ug pCMV-SB+24 ug, 20 ug, 0 ug pcDNA3 (○, ●, ,), respectively. FIG. 1B) Average serum HAAT levels over time in the absence of terminal repeat (TR) sequences. 25 ug phAAT, which lacks terminal repeat sequences, was delivered systemically in combination with 25 ug pcDNA3 (—), 5 ug pCMV-mSB+20 ug pcDNA3 ( ), or 5 ug pCMV-SB+20 ug pcDNA3 (●). FIG. 1C) Long-term serum factor IX concentrations in mice following injection of transposon DNA. 25 ug pTEF1α-hFIX was administered with 5 ug pCMV-SB(●) or 5 ug pCMV-mSB ( ).

Results of these studies demonstrate that active transposase can enhance long-term expression of genes flanked by terminal repeat sequences, resulting in significantly higher serum hAAT levels over a period of more than 3 months compared to mice receiving either no transposase or a functionally-null mutant transposase (FIGS. 1A–C). Similar results were obtained with a 5.4-kb transposon containing the human factor IX cDNA (2.1-kb) under the control of the elongation factor 1-alpha (EF1α) cellular promoter (FIG. 1C). Interestingly, the levels of persistent reporter gene expression observed in vivo decreased with increasing doses of pCMV-SB (FIG. 1A). The fact that identical doses of active and mutant transposase (5 ug pCMVSBk vs. 5 ug pCMV-mSB) produced such different expression profiles suggests that the dosage effect observed in vivo in not likely immune-related. One possible explanation we cannot exclude is that Sleeping Beauty, like the mariner transposase, may be subject to an unusual regulatory phenomenon known as overproduction inhibition, which results in a net reduction in transposase activity at transposase levels exceeding some threshold. In spite of this uncertainty, these studies clearly demonstrate that Sleeping Beauty can maintain significant levels of therapeutic gene expression from non-viral, transposon-based vectors in the mouse.

IV. Histological Examination of Transposon-Based Gene Expression in the Mouse.

Plasmid DNA was administered to immunodeficient C57B1/6-scid mice 8 weeks of age by tail vein injection. Mice received either 25 ug of the donor plasmid pTRSV-βgeo, which contains a 6.0 Kb transposon encoding a cytoplasmic βGal-neomycin fusion protein, or an identical plasmid lacking 5' and 3' TR sequences (pRSV-βgeo). All mice were co-injected with 2.5 ug pCM V-SB or pCMV-mSB, as well as various amounts of pcDNA3 (InVitrogen) to maintain the total plasmid dosage equal to 50 ug/mouse. Mouse tissues (liver, kidney, spleen, heart, lung and brain) were harvested 2 days (n=9) and 35 days (n=18) after plasmid administration, sectioned, stained with X-gal solution and examined under the light microscope to determine the percent of X-gal positive cells/field. Analysis of tissue sections obtained two days after vector administration showed reporter gene expression to be primarily in the liver (approximately 40% of mouse hepatocytes were X-gal$^+$), with little to no expression in heart, kidney, lung, spleen or brain (<0.01%). More importantly, gene expression in the liver was found to persist for at least four weeks in 2–4% of mouse hepatocytes in the presence of active transposase compared with <0.01% in mice which received either non-functional transposase or a reporter gene lacking terminal repeats. Therefore, we estimate that transposons undergo transposition into transcriptionally active regions of mammalian chromosomes in about 5% of mouse hepatocytes.

V. Sleeping Beauty Mediates Genomic Integration of Transposons in Mice.

Figure 2A:
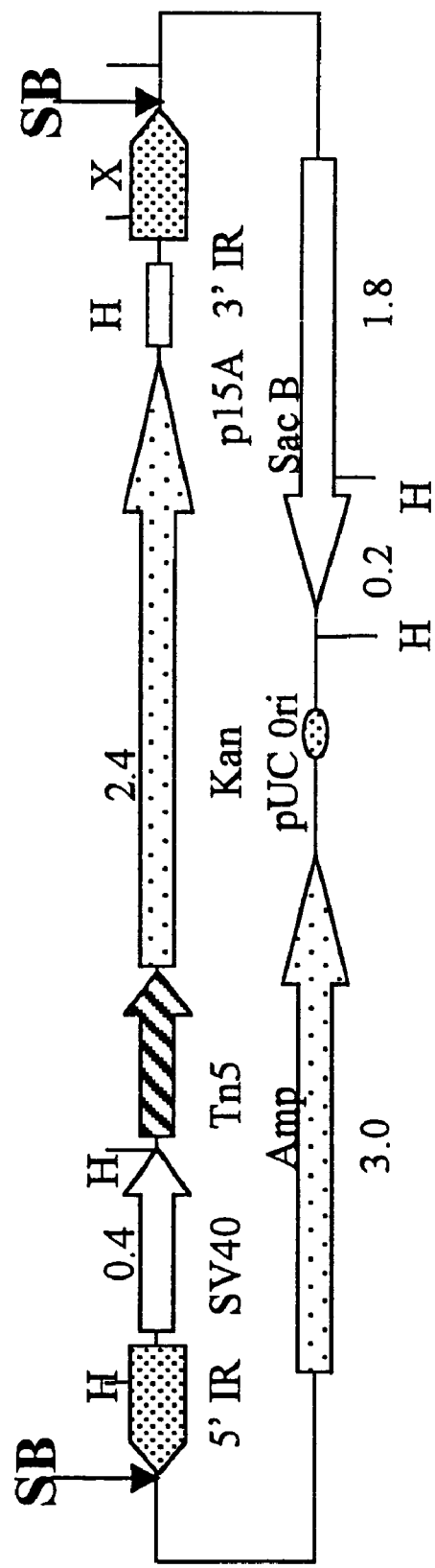
FIGS. 2A to 2B provide figures showing various aspects of the integration assay described in the experimental section, infra.
Figure 2B:
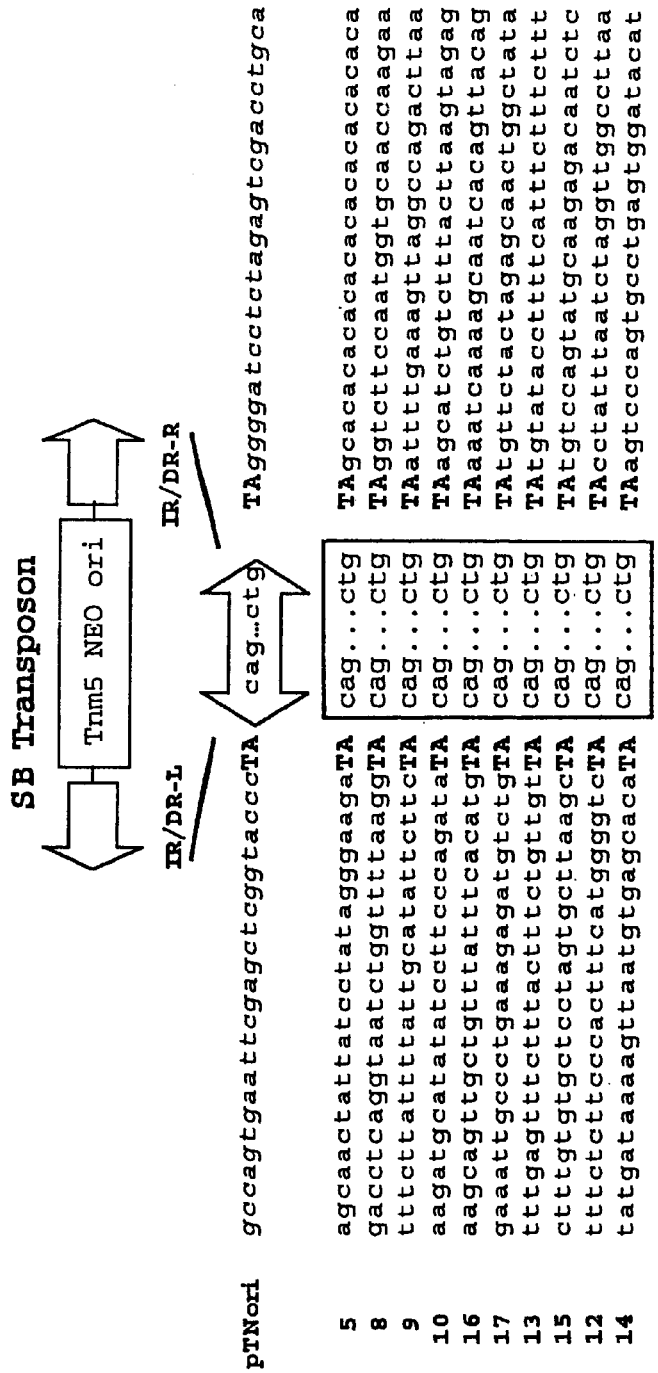

FIG. 2A) Structural components of pTNorisacB vector used for transposon recovery. IR, inverted terminal repeats; SV40 mammalian promoter; Tn5 bacterial promoter; kan, kanamycin resistance gene; p15A origin of replication; Amp, ampicilllin resistance gene; sacB, *Bacillus subtilis* sacB gene for counterselection. H, Hind III; X, Xba I. Numbers represent distances between neighboring Hind III sites. C57B1/6 mice were injected with 25 ug pTNoriSacB and 2.5 ug pCMV-SB plasmids and sacrificed 27 days later. Total liver DNA was phosphatase treated, digested with NheI, SpeI and XbaI restriction endonucleases, self-ligated under dilute conditions, transformed into DH10B electrocompetent cells (GIBCO), and selected for Kan$^R$/Amp$^S$ growth before isolation of plasmid DNA. Transposon DNA analysis by Hind III digestion and ethidium bromide gel electrophoresis shows that each recovered clone contains two bands (2.5-kb and 0.4-kb) corresponding to internal vector sequences, as well as a variety of novel bands that are indicative of transposition. FIG. 2B) Transposon insertion site sequences for SB-mediated transposition into the mouse genome. The DNA flanking the 5' and 3' terminal repeats of the transposon were sequenced using primers IR-1 (5'-AGATGTCCTAACTGACTTGCC) (SEQ ID NO:08) and IR-2 (5'-GTGGTGATCCTAACTGACCTT) (SEQ ID NO:09), respectively. The pUC19 sequences present in the donor plasmid backbone are shown in italics, the transposon sequences are in the central box, and the target site duplications marking the boundary between transposon and mouse sequences are shown in bold type. The dotted lines emanating from clone #2 illustrate the duplication of the TA dinucleotide that occurred in vivo following transposon insertion into the ampicillin gene of pTNoriSacB. These results, which showed each end of the transposon to be flanked by a TA dinucleotide ($11/11$) and sequences not present in the donor plasmid DNA ($10/11$), demonstrate that Sleeping Beauty can mediate transposition of foreign genes into the TA dinucleotides of multiple non-coding regions of the mouse genome.

VI. Transposon-based Gene Therapy in Hemophilia B Mice.

25 ug of the plasmid pT-EF1α-hFIX was delivered to the liver of approximately 20 g adult factor IX deficient mice with 1 ug pCMV-SB or pCMV-mSB by tail vein administration. Plasma hFIX levels were determined periodically by ELISA. Whole blood clotting times (WBCT) were determined by transecting the tail and measuring the time required to clot. For mice whose blood did not clot, blood was collected for 30 min or until 300 ul had been collected, at which time the tails were cauterized.

Human FIX levels were undetectable (<1.5 ng/ml) in mice injected with pCMV-mSB (n=3), whereas mice receiving pCMV-SB (n=3) had human FIX levels ranging from 77 ng/ml to 105 ng/ml. To ascertain whether vector re-administration enhances stable human FIX levels, we re-injected these mice as before and determined the serum human FIX concentrations after seven weeks (day 102 of the study). Mice re-injected with pCMV-SB now had stable human FIX levels ranging from 189 ng/ml to 452 ng/ml, corresponding to a fourfold increase in stable human FIX, whereas human FIX levels in mice re-injected with pCMV-mSB remained undetectable. Therefore, vector re-administration enhances persistent transgene expression in vivo.

We assessed bleeding times in treated mice after transection of their tails. Results showed that mice treated with pCMV-SB exhibited a long-term reduction in their bleeding times (4–7 mm; n=3) compared with animals treated with pCMV-mSB (>30 min; n=3). These data indicate that transposition mediated by Sleeping Beauty can sustain the production of biologically active FIX protein, resulting in partial correction of the bleeding diathesis in a mouse model of hemophilia B.

VII. Additional Experiments

A. Methods

Methylation Status of Transposon DNA in Mouse Livers

We purified pThAAT vector from dam+bacteria and injected it (25 μg) into C57B1/6 mice together with 1 μg of either pCMV-SB (n=6 mice) or pCMV-mSB(n=3 mice). Ten months after vector administration, we performed a surgical ⅔ partial hepatectomy in order to facilitate demethylation of DpnI recognition sites within integrated copies of the transposon. Forty-five days later, mice were sacrificed and liver DNA prepared by salting out. For Southern blot analyses, we digested 10 μg mouse liver DNA with DpnI, HindIII, or DpnI/HindIII separated it on an agarose gel by ethidium bromide gel electrophoresis, and transferred it to nitrocellulose. Membranes were hybridized to a radiolabelled 1.7-kb hAAT fragment and subjected to autoradiography.

Assessing Transposase-Mediated Toxicity in vitro and in Mice

We tested whether transposase activity was toxic to cells in vitro by a transient transfection assay. We seeded 5×10⁵ HeLa cells in 6-well dishes 24 h before transfecting them with 3 μg pCMV-SB, 3 μg pCMV-mSB, 1.5 μg pCMV-SB+ 1.5 μg pTneo, or 1.5 μg pCMV-mSB+1.5 μg pTneo using Superfect (Qiagen). Cells were trypsinized 48 h later, mixed with an equal volume Trypan Blue, and counted under a light microscope using a hemocytometer. All transfections were done in triplicate to demonstrate reproducibility.

We tested whether transposase expression and/or its enzymatic activity resulted in toxicity in vivo by injecting C57B1/6-scid mice (n=4 mice per group) with saline alone, 1 μg pCMV-SB, 25 μg pCMV-SB, 1 μg pCMV-mSB, or 25 μg pCMV-mSB. We assessed liver injury in treated mice by analyzing serum glutamic pyruvic transaminase (SGPT) levels every other day for 14 days using a calorimetric assay.

Transposase Overproduction Inhibition in vivo

We used the polymerase chain reaction (PCR) to analyze liver DNA from C57B1/6-scid mice that had been injected with 25 μg pThAAT alone, or together with 1 μg pCMV-mSB, 25 μg pCMV-mSB, 1 μg pCMV-SB, or 25 μg pCMV-SB. For the amplification of transposon excision-repair products, we added 500 ng mouse liver DNA and 50 pmol each of primers pUC-1 (5'-TACGCCAGCTGGCGAAAG) (SEQ ID NO: 10) and pUC-2 (5'-AGCTCSCTCATTAGGCAC) (SEQ ID NO:11) to a total of 25 μL in Ready-To-Go PCR Beads (Amersham). PCR products were amplified using the following program: 94° C. (5 min) [35 cycles of 94° C. (1 min) 55° C. (30 sec) 72° C. (45 sec)], and 72° C. (7 min). PCR products were analyzed on a 2% agarose gel by ethidium bromide gel electrophoresis.

Assessing Vector Re-administration In Vivo

We injected C57B1/6 mice via the tail vein with 1 μg pCMV-SB and either 25 μg pThAAT (n=8) or 25 μg pTEF1α-hFIX (n=8). Approximately 1 month later, we injected hAAT mice with 1 μg pCMV-SB and 25 g pTEF1α-hFIX, and hFIX mice with 1 μl pCMV-SB and 25 μg pThAAT. Following each plasmid injection, we periodically measured serum hAAT and hFIX levels by an ELISA assay.

Co-Labeling Mouse Hepatocytes for BrdU Incorporation and β-Galactosidase

We infused C57B1/6-scid mice with 25 μg pTβgeo and 1 μg pCMV-SB plasmids by tail vein injection, and then inserted a subcutaneous osmotic minipump to deliver BrdU (1 mg/d) for 7 days. Thirty-three days later, mice were sacrificed and their livers fixed in 4% paraformaldehyde. We mounted 10 μm sections onto glass slides and stained tissue with 5-bromo-4-chloro-3-indolyl β-D-galactosidase (X-gal) overnight at 37° C. The next day, we removed endogenous peroxidase activity by incubating tissues for 30 min in 0.3% hydrogen peroxide, and then blocked in 10% normal rabbit serum (Vector labs) overnight at 4° C. We incubated tissue sections with primary antibody against BrdU (1:400) for 1 h and secondary antibody (1:500) for 30 min. We used 3'-3'-diaminobenzidine (DAB; Sigma) as the brown substrate for precipitation of the BrdU sample. The tissue sections were then counterstained with hematoxylin, dehydrated and coverslipped for BrdU and X-gal analyses under a light microscope.

B. Results

Transcriptionally Active Transposons are Predominantly Integrated into the Genome Following a single administration of pThAAT and pCMV-SB, mice stably expressed ~2500 ng/ml serum hAAT for a period of 10 months. This level of gene expression was several fold higher than mice receiving pThAAT and pCMV-mSB, indicating that transgene expression in mice receiving wild-type transposase had originated primarily from integrated copies of the transposon and not from plasmid-based episomes. If this were true, then inducing hepatocyte proliferation would be expected to have little-to-no effect on transgene levels in mice injected with pCMV-SB. To test this hypothesis, we subjected treated mice to a ⅔ surgical partial hepatectomy (PH), which stimulates hepatocellular regeneration such that almost all hepatocytes divide once or twice, and then monitored the effect this had on transgene levels over time. Specifically, C57B1/6 mice were injected with 25 mg pThAAT+1 mg pCMV-SB (Δ) (n=6 mice), or 25 mg pThAAT+1 mg pCMV-mSB (Δ) (n=3 mice) and their serum hAAT levels monitored by ELISA. Liver regeneration was induced 10 months after vector administration by surgically removing ⅔ of the mouse liver under anesthesia. During a 4 week time period after PH, transgene expression remained essentially unchanged in mice treated with active transposase but fell sharply in pCMV-mSB-injected control mice. These results suggest that transcriptionally active transposons in pCMV-SB-injected mice are predominantly integrated into the mouse genome.

To confirm these findings, we performed Southern blot analysis using the restriction endonuclease DpnI to differentiate between episomal and integrated forms of transposon DNA in these mice. This enzyme recognizes the methylated sequence GmATC, which is present eight times within the previously injected hAAT transposon. In preliminary studies, DpnI treatment was shown to completely chew-up the injected methylated vector DNA, but had no effect on an unmethylated control vector. Since two rounds of hepatocyte replication should be sufficient to unmethylate DpnI sites contained within a chromosomal element, we tested whether any amount of transposon DNA in pCMV-SB-injected animals was now resistant to DpnI digestion. Samples from six mice treated with pCMV-SB showed an average of 0.25 copies of DpnI-resistant transposon DNA per diploid liver genome, whereas samples from three control mice were found to be fully DpnI-sensitive. Subtracting this value from the total copy number we obtained with the 2-cutter HindIII (~1 copy/liver diploid genome;), integrated transposons must therefore represent ~25% of the total vector genomes in these mice. Furthermore, based on the finding that 75% of the vector remained DpnI-sensitive in pCMV-SB-injected animals, and 100% in pCMV-mSB-injected mice, we conclude that the original input DNA can persist within the mouse liver as a replication-deficient episome for at least 10 months. However, for reasons that are still under investigation, these episomes remain predominantly transcriptionally inactive and thus do not contribute significantly to the total serum hAAT levels detected in pCMV-SB-injected mice.

Absence of Detectable Transposase Toxicity in vitro and in vivo

To determine whether there was any toxicity associated with either transposase expression or its catalytic activity, we transfected HeLa cells with pCMV-SB or pCMV-mSB either alone, or together with the transposon pTneo. We then determined the percentage of viable cells 3 days later by Trypan Blue exclusion. The observed results demonstrated that irrespective of the presence of a specific transposon substrate, cells expressing active transposase remained equally viable as cells expressing inactive transposase. Therefore, transposase activity is not cytotoxic in vitro under these experimental conditions.

To determine whether or not the same was also true in vivo, we co-injected mice with pThAAT and different doses of pCMV-SB or pCMV-mSB, and then monitored the levels of serum glutamic pyruvic transaminase (SGPT), a sensitive measure of liver injury. During the two-week period immediately following plasmid administration, we observed similar SGPT levels under each experimental condition (we compared 0 µg, 1 µg and 25 µg pCMV-SB and pCMV-mSB) (C57Bl/6-scid mice (n=4 mice per group) were injected with saline alone (—), 1 mg pCMV-SB(1), 25 mg pCMV-SB (m), 1 mg pCMV-mSB (s), or 25 mg pCMV-mSB (Δ). After vector administration, livery injury was assessed by periodically determining serum glutamic pyruvic transaminase (SGPT) levels using a colorimetric assay). No evidence was found either in vitro or in vivo that would indicate that transposase activity is detrimental to a transfected cell. Based on these findings, we further conclude that transposase-mediated toxicity must also not contribute significantly to the profound reduction in transgene levels observed in animals injected with higher pCMV-SB doses.

The SB Transposase Exhibits Overproduction Inhibition in vivo

Recently, it has been reported that increased doses of the Himar1 transposase and the Mos1 element can effectively down-regulate transposition of these mariner-like elements in vitro and in *Drosophila melanogaster*, respectively. This phenomenon, called overproduction inhibition, is thought to be an inherent regulatory mechanism that minimizes damage to a host organism by an autonomous transposable element. This suggests that high-level transposase expression might be inhibiting Sleeping Beauty's enzymatic activity in vivo. To test this hypothesis, we developed a polymerase chain reaction (PCR)-based strategy to monitor transposase function in vivo under a variety of experimental conditions. This approach utilizes a pair of flanking primers which, after excision of the 2.8-kb HAAT transposon and double-strand break repair, will amplify a much smaller 271 bp PCR product, the amount of which indicates the relative level of transposase activity under each experimental condition. Using this strategy, we analyzed liver DNA samples from immune-deficient mice injected with pThAAT and different doses of pCMV-SB or pCMV-mSB as a control. Results demonstrate that transposon excision is significantly reduced in mice receiving a 25 µg dose of pCMV-SB compared to a 1 µg dose. Therefore, overproduction inhibition is likely a shared feature of mariner and Tc1-like elements.

Transposon Expression is Stable After Vector Readministration in vivo

Figure 3:
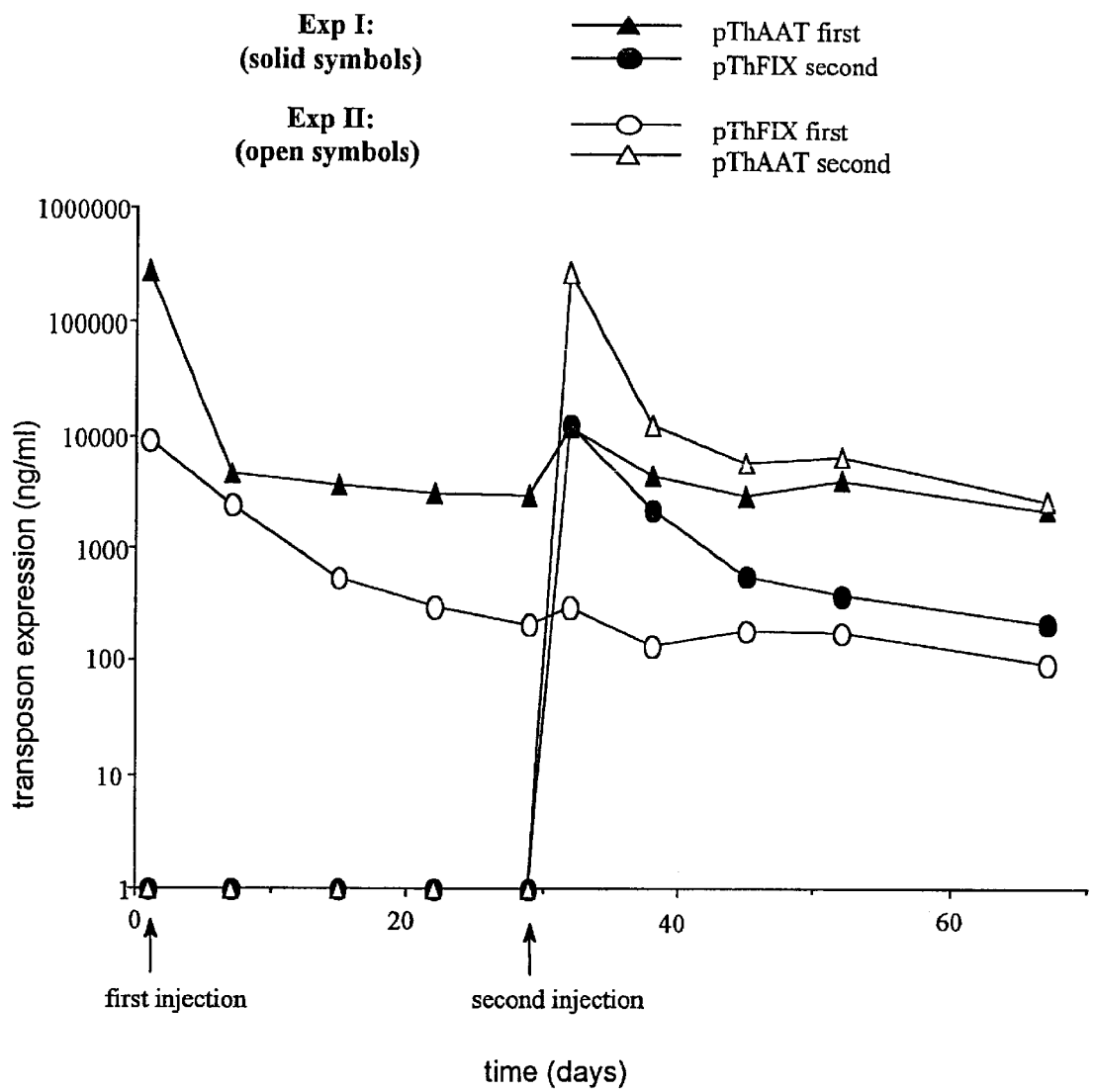
FIG. 3 provides the results of study reported in the experimental section, infra, showing efficacy of vector re-administration in vivo.

The previous study demonstrated that vector re-administration could be used to increase persistent transgene expression in vivo. Although this could conceivably be used to obtain therapeutic ranges of a clinically relevant protein in vivo, it raises new important questions regarding the stability of endogenous elements during periods of transposase re-expression. Therefore, to investigate whether transposase re-administration had any effect on the expression of a non-autonomous transposon contained within the host genome, we first injected mice with pCMV-SB and either pThAAT or pThFIX into mouse tail veins and monitored their serum reporter levels over time. Approximately one month later, serum transgene levels these mice had stabilized. At this time, we re-injected these mice with pCMV-SB together with a secondary transposon (pThAAT mice received pThFIX, and pThFIX mice pThAAT) and then monitored expression of both reporters by serum ELISA for an additional five weeks. Results are shown in FIG. 3. In FIG. 3, C57Bl/6 mice (n=6 mice per group) were injected first with 1 mg pCMV-SB+25 mg pThAAT (s) or 1 mg pCMV-SB+25 mg pThFIX (m) and again 1 month later. For the second injection, mice stably expressing hAAT were injected with 1 mg pCMV-SB and 25 mg pThFIX (1), and mice FIX-expressing mice were infused with 1 mg pCMV-SB+25 mg pThAAT (Δ). Transposon expression was monitored periodically by serum ELISA. The observed results demonstrate that re-expression of transposase can catalyze efficient transposition of a secondary transposon in mouse livers without significantly changing expression from endogenous elements. Consistent with these data, Luo et al recently reported that chromosomal transposition of a Sleeping Beauty-based element was inefficient in mouse embryonic stem (ES) cells ($\sim 1 \times 10^{-6}$), although transposition efficiencies did vary according to the chromosomal locale of the particular transpon. Together, these data suggest that transposition from a chromosome is much less efficient than from a supercoiled plasmid both in vitro and in vivo. Although the reason for these differences remains under investigation, the reduced mobilization of endogenous elements suggests that vector re-administration is tolerable in vivo.

Cell-Cycling is Not Required for Transposition in vivo

All current integrating vectors appear to require cell cycling for efficient in vivo gene transfer to quiescent liver cells. These include murine-leukemia-based retroviruses (MLV) and human-immunodeficiency (HIV)-based lentiviral vectors. Therefore, we determined if there were any cell-cycle requirements for SB-mediated transposition in mouse hepatocytes. To do this, we infused C57B1/6-scid mice with pCMV-SB and pTβgeo, which contains a transposon encoding cytoplasmic β-galactosidase, and then labeled proliferating nuclei by inserting a mini osmotic pump subcutaneously to deliver 5'-bromo-2'-deoxyuridine (BrdU; 1 mg/d) for seven days. In an untreated mouse, ~1% hepatocytes should normally be BrdU-labeled. However, when we analyzed liver tissue from these mice 5 weeks after vector administration, we observed tenfold more BrdU-positive hepatic nuclei compared to untreated mice. This increase in the number of cycling hepatocytes is likely the result of hepatocellular regeneration that occurred in response to the acute liver toxicity following a rapid tail vein injection. More importantly, we found that only ~5% of X-gal-positive hepatocytes were co-labeled with BrdU. Therefore, since cytosolic β-gal expression should only be detected in cells that have undergone stable transposition under these experimental conditions, DNA synthesis must not be required for efficient transposition in the liver.

It is evident from the above results and discussion that the subject invention provides an important new method for inserting nucleic acids into the genomes of cells of multicellular organisms. Use of the Sleeping Beauty transposase system according to the subject methods provides for the ability to achieve stable integration of the a nucleic acid into the genome of one or more target cells by administration of vectors directly to the multicellular organism. In other words, the subject methods provide in vivo methods of integrating nucleic acids into the genomes of target cells. As such, the subject methods have wide ranging application, including in the field of gene therapy. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of integrating an exogenous nucleic acid into the genome of at least one hepatic cell of a multicellular organism, said method comprising:

administering directly to said multicellular organism:
(a) a Sleeping Beauty transposon comprising said exogenous nucleic acid flanked by a first inverted repeat sequence having a sequence of SEQ ID NO:18 and a second inverted repeat sequence having a sequence of SEQ ID NO:19; and
(b) a source of Sleeping Beauty transposase activity that has a sequence of SEQ ID NO:01;

to integrate said nucleic acid into said genome.

2. The method according to claim 1, wherein said source of Sleeping Beauty transposase activity comprises a nucleic acid encoding a protein having Sleeping Beauty transposase activity.

3. The method according to claim 1, wherein said transposon and source of transposase activity are present on separate vectors.

4. The method according to claim 1, wherein said transposon and source of transposase activity are present on the same vector.

5. The method according to claim 1, wherein said multicellular organism is a vertebrate.

6. The method according to claim 1, wherein said administering is administering systemically.

7. A method of inserting an exogenous nucleic acid into the genome of at least one hepatic cell of a mammal, said method comprising:

administering directly to said mammal:
(a) a Sleeping Beauty transposon comprising said exogenous nucleic acid flanked by a first inverted repeat sequence having a sequence of SEQ ID NO:18 and a second inverted repeat sequence having a sequence of SEQ ID NO:19; and
(b) a source of a Sleeping Beauty transposase activity that has a sequence of SEQ ID NO:01;

to insert said exogenous nucleic acid into said genome.

8. The method according to claim 7, wherein said source of Sleeping Beauty transposase activity comprises a nucleic acid encoding a protein having Sleeping Beauty transposase activity.

9. The method according to claim 7, wherein said Sleeping Beauty transposon and said source of Sleeping Beauty transposase activity are present on separate vectors.

10. The method according to claim 7, wherein said Sleeping Beauty transposon and said source of Sleeping Beauty transposase activity are present on the same vector.

11. The method according to claim 7, wherein said exogenous nucleic acid comprises a gene.

12. The method according to claim 7, wherein said administering is administering systemically.

13. A method for expressing an exogenous gene in at least one hepatic cell of a multicellular organism, said method comprising:

administering directly to said organism:
(a) a Sleeping Beauty transposon comprising said exogenous gene flanked by a first inverted repeat sequence having a sequence of SEQ ID NO:18 and a second inverted repeat sequence having a sequence of SEQ ID NO:19; and
(b) a source of Sleeping Beauty transposase activity that has a sequence of SEQ ID NO:01;

to integrate said gene into the genome of at least one hepatic cell of said multicellular organism and expressed therein so that said exogenous gene is expressed in said at least one cell of said multicellular organism.

14. The method according to claim 13, wherein said source of Sleeping Beauty transposase activity comprises a nucleic acid encoding said transposase.

15. The method according to claim 13, wherein said Sleeping Beauty transposon and said source of Sleeping Beauty transposase activity are present on separate vectors.

16. The method according to claim 13, wherein said Sleeping Beauty transposon and said source of Sleeping Beauty transposase activity are present on the same vector.

17. The method according to claim 13, wherein said multicellular organism is a vertebrate animal.

18. The method according to claim 17, wherein said vertebrate animal is a mammal.

19. The method according to claim 13, wherein said administering is administering systemically.

20. A method for expressing in a multicellular organism, said method comprising:
    administering directly to said organism:
    (a) a Sleeping Beauty transposon comprising a gene encoding said protein flanked by a first inverted repeat sequence having a sequence of SEQ ID NO:18 and a second inverted repeat sequence having a sequence of SEQ ID NO:19; and
    (b) a source of Sleeping Beauty transposase activity that has a sequence of SEQ ID NO:01;
    to integrate said gene into the genome of at least one hepatic cell of said multicellular organism so that said protein is expressed in said multicellular organism.

21. The method according to claim 20, wherein said source of Sleeping Beauty transposase activity comprises a nucleic acid encoding said transposase.

22. The method according to claim 20, wherein said Sleeping Beauty transposon and said source of Sleeping Beauty transposase are present on separate vectors.

23. The method according to claim 20, wherein said Sleeping Beauty transposon and bid source of Sleeping Beauty transposase are present on the same vector.

24. The method according to claim 20, wherein said multicellular organism is a vertebrate animal.

25. The method according to claim 24, wherein said vertebrate animal is a mammal.

26. The method according to claim 20, wherein said multicellular organism comprises substantially no amount of said protein prior to said administering step.

27. The method according to claim 20, wherein said multicellular organism comprises at least some amount of said protein prior to said administering step.

28. The method according to claim 20, wherein said administering is administering systemically.

29. A method of in vivo transfer of a gene into the genome of at least one cell of a multicellular organism, said method comprising:
    administering directly to said multicellular organism:
    (a) a Sleeping Beauty transposon comprising said gene flaked by a first inverted repeat sequence having a sequence of SEQ ID NO:18 and a second inverted repeat sequence having a sequence of SEQ ID NO:19; and
    (b) a source of a Sleeping Beauty transposase activity that has a sequence of SEQ ID NO:01;
    to transfer said gene into said genome.

30. The method according to claim 29, wherein said source of Sleeping Beauty transposase activity comprises a nucleic acid encoding a protein having Sleeping Beauty transposase activity.

31. The method according to claim 29, wherein said Sleeping Beauty transposon and said source of Sleeping Beauty transposase activity are present on separate vectors.

32. The method according to claim 29, wherein said Sleeping Beauty transposon and said source of Sleeping Beauty transposase activity are present on the same vector.

33. The method according to claim 29, wherein said administering is administering systemically.

* * * * *